(12) United States Patent
Germain et al.

(10) Patent No.: US 10,441,353 B2
(45) Date of Patent: *Oct. 15, 2019

(54) TISSUE EXTRACTION DEVICES AND METHODS

(71) Applicant: BOSTON SCIENTIFIC SCIMED, INC., Maple Grove, MN (US)

(72) Inventors: Aaron Germain, Campbell, CA (US); Kyle Klein, San Jose, CA (US); Benedek Orczy-Timko, Budapest (HU); John H. Shadduck, Menlo Park, CA (US); Michael D. Walker, Mountain View, CA (US); Csaba Truckai, Saratoga, CA (US); Balazs Lesko, Budapest (HU)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 2 days.

This patent is subject to a terminal disclaimer.

(21) Appl. No.: 15/816,423

(22) Filed: Nov. 17, 2017

(65) Prior Publication Data
US 2018/0071015 A1 Mar. 15, 2018

Related U.S. Application Data

(63) Continuation of application No. 15/460,810, filed on Mar. 16, 2017, now Pat. No. 9,839,473, which is a
(Continued)

(51) Int. Cl.
*A61B 18/18* (2006.01)
*A61B 18/14* (2006.01)
(Continued)

(52) U.S. Cl.
CPC .... *A61B 18/1485* (2013.01); *A61B 17/32002* (2013.01); *A61B 18/1482* (2013.01);
(Continued)

(58) Field of Classification Search
CPC ......... A61B 18/18; A61B 17/32; A61B 18/14; A61B 17/3205; A61B 17/320016;
(Continued)

(56) References Cited

U.S. PATENT DOCUMENTS

| 4,650,462 A | 3/1987 | DeSatnick et al. |
| 4,735,603 A | 4/1988 | Goodson et al. |

(Continued)

FOREIGN PATENT DOCUMENTS

| EP | 2100567 A1 | 9/2009 |
| GB | 2327351 A | 1/1999 |

(Continued)

OTHER PUBLICATIONS

AAGL Practice Report: Practice Guidelines for the Management of Hysteroscopic Distending Media: (Replaces Hysteroscopic Fluid Monitoring Guidelines. J Am Assoc Gynecol Laparosc. 2000;7: 167-168) J Minim Invasive Gynecol. Mar.-Apr. 2013;20:137-48. doi: 10.1016/j.jmig.2012.12.002.

(Continued)

*Primary Examiner* — John Eric C Morales
(74) *Attorney, Agent, or Firm* — Seager, Tufte & Wickhem, LLP

(57) ABSTRACT

The tissue cutting device comprises an elongated assembly including both an outer sleeve and an inner sleeve. The outer sleeve has a tissue-receiving window, and the inner sleeve has a distal end which cuts tissue as the inner sleeve is advanced past the window. The tissue is received into a lumen of the inner sleeve, and the inner sleeve lumen is typically enlarged in a proximal direction to reduce the tendency of resected tissue to lodge therein. The tissue displacement member is optionally provided at a distal end (Continued)

of the outer sleeve to further aid in dislodging tissue which becomes captured in a distal end of the inner sleeve of the lumen.

20 Claims, 13 Drawing Sheets

Related U.S. Application Data continuation of application No. 14/623,186, filed on Feb. 16, 2015, now Pat. No. 9,636,170, which is a continuation of application No. 13/531,309, filed on Jun. 22, 2012, now Pat. No. 8,974,448.

(60) Provisional application No. 61/501,101, filed on Jun. 24, 2011.

(51) Int. Cl.
*A61B 17/32* (2006.01)
*A61B 18/00* (2006.01)

(52) U.S. Cl.
CPC ... *A61B 18/18* (2013.01); *A61B 2017/320028* (2013.01); *A61B 2018/00083* (2013.01); *A61B 2018/00196* (2013.01); *A61B 2018/00559* (2013.01); *A61B 2018/00601* (2013.01); *A61B 2018/00982* (2013.01); *A61B 2018/142* (2013.01); *A61B 2218/002* (2013.01); *A61B 2218/007* (2013.01)

(58) Field of Classification Search
CPC ............ A61B 18/1482; A61B 18/1485; A61B 17/32002; A61B 18/042; A61B 2017/00269; A61B 2018/00196; A61B 2018/00559; A61B 2018/00595
USPC ..................................... 606/33, 46, 119, 167
See application file for complete search history.

(56) References Cited

U.S. PATENT DOCUMENTS

| | | | |
|---|---|---|---|
| 5,098,375 A | 3/1992 | Baier | |
| 5,106,364 A | 4/1992 | Hayafuji et al. | |
| 5,277,696 A | 1/1994 | Hagen et al. | |
| 5,382,229 A | 1/1995 | Grabenkort et al. | |
| 5,437,629 A | 8/1995 | Goldrath | |
| 5,643,203 A | 7/1997 | Beiser et al. | |
| 5,669,921 A | 9/1997 | Berman et al. | |
| 5,730,752 A | 3/1998 | Alden et al. | |
| 5,810,858 A | 9/1998 | Berman et al. | |
| 5,823,990 A | 10/1998 | Henley et al. | |
| 5,830,180 A | 11/1998 | Chandler et al. | |
| 5,853,392 A | 12/1998 | Dennis | |
| 5,906,615 A | 5/1999 | Thompson | |
| 5,925,050 A | 7/1999 | Howard, III | |
| 6,032,673 A | 3/2000 | Savage et al. | |
| 6,109,268 A | 8/2000 | Thapliyal et al. | |
| RE36,914 E | 10/2000 | Carlsen et al. | |
| 6,206,014 B1 | 3/2001 | Cameron, III et al. | |
| 6,245,084 B1 | 6/2001 | Mark et al. | |
| 6,358,263 B2 | 3/2002 | Mark et al. | |
| 6,629,986 B1 | 10/2003 | Ross et al. | |
| 6,979,332 B2 | 12/2005 | Adams | |
| 7,029,451 B2 | 4/2006 | Anderson et al. | |
| 7,070,604 B1 | 7/2006 | Garito et al. | |
| 7,204,821 B1 | 4/2007 | Clare et al. | |
| 7,226,459 B2 | 6/2007 | Cesarini et al. | |
| 7,384,417 B2 | 6/2008 | Cucin | |
| 7,549,987 B2 | 6/2009 | Shadduck | |
| 7,674,259 B2 | 3/2010 | Shadduck | |
| 7,892,229 B2 | 2/2011 | Shadduck et al. | |
| 8,313,485 B2 | 11/2012 | Shadduck | |
| 8,512,326 B2 | 8/2013 | Shadduck et al. | |
| 8,728,066 B2 | 5/2014 | Shadduck et al. | |
| 8,974,448 B2* | 3/2015 | Germain ......... | A61B 17/32002 606/32 |
| 9,254,142 B2* | 2/2016 | Germain ........ | A61B 17/320016 |
| 2002/0010463 A1 | 1/2002 | Muller et al. | |
| 2002/0072745 A1 | 6/2002 | Truckai et al. | |
| 2003/0060862 A1 | 3/2003 | Goble et al. | |
| 2004/0049217 A1 | 3/2004 | Ross et al. | |
| 2004/0092980 A1 | 5/2004 | Cesarini et al. | |
| 2004/0102770 A1 | 5/2004 | Goble | |
| 2004/0167427 A1 | 8/2004 | Quick et al. | |
| 2004/0167428 A1 | 8/2004 | Quick et al. | |
| 2004/0267255 A1 | 12/2004 | Auge, II et al. | |
| 2005/0096649 A1 | 5/2005 | Adams | |
| 2005/0236329 A1 | 10/2005 | Brotherton et al. | |
| 2006/0047185 A1 | 3/2006 | Shener et al. | |
| 2006/0135955 A1 | 6/2006 | Shadduck | |
| 2006/0224154 A1 | 10/2006 | Shadduck et al. | |
| 2007/0016182 A1 | 1/2007 | Lipson et al. | |
| 2007/0021713 A1 | 1/2007 | Kumar et al. | |
| 2007/0036768 A1 | 2/2007 | Fraser et al. | |
| 2007/0088275 A1 | 4/2007 | Stearns et al. | |
| 2007/0244353 A1 | 10/2007 | Larsen | |
| 2008/0039832 A1 | 2/2008 | Palanker et al. | |
| 2008/0065060 A1 | 3/2008 | Ein-Gal | |
| 2008/0091061 A1 | 4/2008 | Kumar et al. | |
| 2008/0091071 A1 | 4/2008 | Kumar et al. | |
| 2008/0287893 A1 | 11/2008 | Ineson | |
| 2009/0082715 A1 | 3/2009 | Charles | |
| 2009/0137943 A1 | 5/2009 | Stearns et al. | |
| 2009/0270898 A1 | 10/2009 | Chin et al. | |
| 2009/0312753 A1 | 12/2009 | Shadduck | |
| 2010/0100091 A1 | 4/2010 | Truckai | |
| 2010/0152533 A1 | 6/2010 | Mark | |
| 2011/0224486 A1 | 9/2011 | Nguyen et al. | |
| 2011/0264090 A1 | 10/2011 | Shadduck et al. | |
| 2011/0306968 A1 | 12/2011 | Beckman et al. | |
| 2012/0053583 A1 | 3/2012 | Palanker et al. | |
| 2012/0271300 A9 | 10/2012 | Shadduck et al. | |
| 2012/0330292 A1 | 12/2012 | Shadduck et al. | |
| 2013/0046304 A1 | 2/2013 | Germain et al. | |
| 2013/0079702 A1 | 3/2013 | Klein et al. | |
| 2013/0103021 A1 | 4/2013 | Germain et al. | |
| 2013/0172805 A1 | 7/2013 | Truckai et al. | |
| 2013/0172870 A1 | 7/2013 | Germain et al. | |
| 2013/0231652 A1 | 9/2013 | Germain et al. | |
| 2013/0296847 A1 | 11/2013 | Germain et al. | |

FOREIGN PATENT DOCUMENTS

| | | |
|---|---|---|
| WO | 2010096139 A2 | 8/2010 |
| WO | 2010096139 A3 | 12/2011 |

OTHER PUBLICATIONS

Liu, et al. Clinical application of hysteriscopic electroresection in 775 cases. Di YHi Jun Yi Da Xue Xue Bao. Apr. 2004;24(4):467-9. (in Chinese with English abstract).

Phillips, et al. The Effect of Dilute Vasopressin Solution on Blood Loss During Operative Hysteroscopy. J Am Assoc Gynecol Laparosc. Aug. 1996;3(4, Supplement):S38.

* cited by examiner

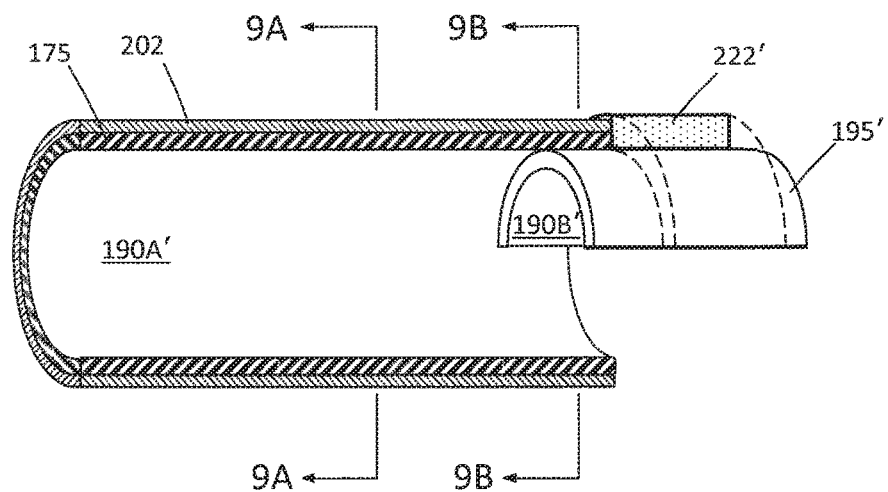
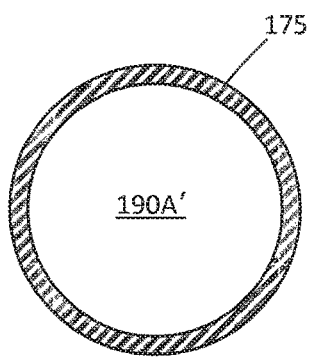 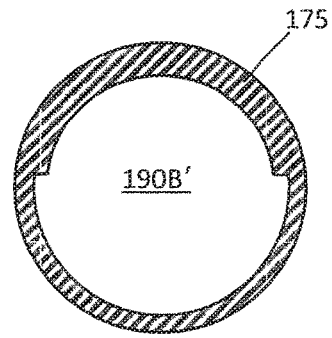
FIG. 8
FIG. 9A    FIG. 9B

TISSUE EXTRACTION DEVICES AND METHODS

CROSS-REFERENCE TO RELATED APPLICATIONS

This application is a continuation of U.S. application Ser. No. 15/460,810, filed Mar. 16, 2017; which is a continuation of U.S. application Ser. No. 14/623,186, filed Feb. 16, 2015, now U.S. Pat. No. 9,636,170; which is a continuation of U.S. application Ser. No. 13/531,309, filed Jun. 22, 2012, now U.S. Pat. No. 8,974,448, which claims the benefit of Provisional Application No. 61/501,101, filed on Jun. 24, 2011, the full disclosures of which are incorporated herein by reference.

FIELD OF THE INVENTION

The present invention relates systems and methods for the cutting and extraction of uterine fibroid tissue, polyps and other abnormal uterine tissue.

BACKGROUND OF THE INVENTION

Uterine fibroids are non-cancerous tumors that develop in the wall of uterus. Such fibroids occur in a large percentage of the female population, with some studies indicating up to 40 percent of all women have fibroids. Uterine fibroids can grow over time to be several centimeters in diameter and symptoms can include menorrhagia, reproductive dysfunction, pelvic pressure and pain.

One current treatment of fibroids is hysteroscopic resection or myomectomy which involves transcervical access to the uterus with a hysteroscope together with insertion of a cutting instrument through a working channel in the hysteroscope. The cutting instrument may be a mechanical tissue cutter or an electrosurgical resection device such as a cutting loop. Mechanical cutting devices are disclosed in U.S. Pat. Nos. 7,226,459; 6,032,673 and 5,730,752 and U.S. Published Patent Appl. 2009/0270898. An electrosurgical cutting device is disclosed in U.S. Pat. No. 5,906,615.

While hysteroscopic resection can be effective in removing uterine fibroids, many commercially available instrument are too large in diameter and thus require anesthesia in an operating room environment. Conventional resectoscopes require cervical dilation to about 9 mm. What is needed is a system that can effectively cut and remove fibroid tissue through a small diameter hysteroscope.

One particular challenge to cutting and removing fibroids using a small diameter hysteroscope is that resected tissue can easily become lodged in the small diameter lumens found in such small scopes. Therefore, it would be particularly useful to provide apparatus and methods which reduce the likelihood of resected tissue becoming lodged in the tissue removal lumens of such small diameter hysteroscopes. At least some of these objectives will be met by the inventions described herein below.

SUMMARY OF THE INVENTION

The present invention provides improved tissue cutting devices, tissue extraction devices, and methods for their use, where the likelihood of resected tissue becoming lodged in the device is greatly reduced. The devices and methods may utilize one or more of a number of separate features, described in details below, where the individual features may be used independently or in combination in order to reduce the likelihood that tissue will become lodged in even very small tissue removal lumens used in hysteroscops and similar recectoscopes.

In a first aspect, a tissue cutting device comprises an elongated assembly including both an outer sleeve and an inner sleeve. The outer sleeve has a tissue-receiving window, typically near its distal end, which is open to an interior lumen of the outer sleeve. The inner sleeve is disposed coaxially in the lumen of the outer sleeve, and the sleeves are arranged so that the inner sleeve can reciprocate within the outer sleeve so that a tissue-cutting distal end of the inner sleeve can be advanced past the tissue-receiving window. In this way, by advancing the inner sleeve relative to the outer sleeve while tissue intrudes into the open window, typically fibroid tissue but other tissues as well, the intruding tissue may then be resected by advancing the inner sleeve to pass the cutting edge over the open window. The resected tissue is received through an open distal end of the inner sleeve into a distal portion of the inner sleeve lumen. Typically, a partial vacuum will be drawn on the inner sleeve lumen, to draw the resected tissue into the inner sleeve lumen. In order to reduce the chance that the resected tissue will become lodged in a distal portion of the inner sleeve lumen, a proximal portion of the inner sleeve lumen is provided with a cross sectional area which is larger than that of the distal portion. The increased in cross-sectional area need not be great, usually being at least 5%, and sometimes being 10% or more greater.

In another aspect of the present invention, the outer sleeve lumen may have a distal lumen portion extending distally of the window. The distal lumen portion will typically have a length which is at least as long as the length of the distal portion of the inner sleeve lumen. In this way, the inner sleeve may be advanced past the tissue-receiving window and into the distal lumen portion of the outer sleeve lumen. Such advancement not only allows a clean cut, it also allows for a displacement feature to be disposed in the distal lumen portion of the outer sleeve to engage and dislodge the tissue in the distal portion of the outer sleeve lumen as the inner sleeve is advanced distally into the distal lumen. The distance from a distal edge of the window to the distal end of the interior passage way will typically be at least 4 mm, often being 6 mm, sometimes being 8 mm or longer. The length of the distal lumen portion will typically be at least 5 mm, often being longer. Usually, the distal portion of the inner sleeve lumen will also have a length of at least 5 mm, typically being substantially the same as the length of the distal lumen portion of the outer sleeve.

The tissue-cutting distal end of the inner sleeve may comprise any conventional tissue-cutting structure, typically being a sharp-edged blade, a radiofrequency (RF) electrode, or the like.

Further optionally, an edge of the window may be surrounded by a dielectric material, typically having a width of at least 0.005 in.

Further optionally, the inner sleeve may have a first stroke portion which advances the tissue-cutting end across the window and a second stroke portion which advances the tissue-cutting end beyond the window, or a length of the second stroke portion is at least 5% of the combined lengths of the first and second stroke portions.

In a further aspect of the present invention, the tissue extraction device comprises a handle and a shaft assembly extending axially from the handle. The shaft assembly has a tissue-receiving window communicating with an interior extraction lumen for extracting tissue. The shaft assembly further comprises axially-extending first and second elements with at least one element being movable relative to the other element to move between a first position and a second position in order to resect tissue received in the window. A displacement feature coupled to the shaft is configured to displace resected tissue from the extraction lumen.

The first position of the first and second elements typically comprises an open-window configuration for receiving tissue therein. The second position is then a closed-window configuration, where movement of the elements from the first position toward the second position typically cuts tissue with a cutting edge on at least one of the elements. The cutting element will typically be a sharp-edged blade, an RF electrode, or the like. In exemplary embodiments, the displacement feature will comprise a projecting element that extends into the extraction lumen so that resected tissue is displaced as the elements are moved relative to each other. The projecting element will physically engage a tissue just after it has been resected and will act as a barrier to dislodge the tissue proximally as the cutting element is advanced further in the distal direction. The displacement feature may have a maximum cross-sectional dimension which is sufficient to extend substantially across a cross-section of the extraction lumen. In other embodiments, the displacement feature will have a cross-sectional area or "footprint" that substantially occupies the cross-section of the extraction lumen. In still other embodiments, the displacement feature may have a shape which is symmetric about a central axis of the extraction lumen but will not necessarily occupy the entire cross-section of the extraction lumen. Specific examples would be axially fluted configurations, star-shaped configurations, and the like. In other specific embodiments, the displacement feature may comprise a dielectric material and may be configured to extend axially into the extraction lumen by a distance of at least 2 mm, sometimes at least 4 mm, and other times at least 6 mm. In still other embodiments, the displacement feature will have a cross-sectional area which is at least 50% of the cross-sectional area of the extraction lumen in the region where the displacement feature enters the lumen.

The present invention also provides methods for cutting and extracting tissue from a body cavity, such as fibroids from a uterus. The methods comprise cutting tissue with a reciprocating inner sleeve having an extending stroke and a retracting stroke within an outer sleeve. The extending stroke cuts and captures tissue received through a tissue-receiving window in the outer sleeve. Tissue which is cut can become captured in a distal portion of a lumen of the inner sleeve, and if it is, the captured tissue is pushed in a proximal direction from the distal portion of the lumen in the inner sleeve where the displacement member, when the cutting sleeve is in a transition range between the extending stroke and the retracting stroke. The displacement member is able to push the captured tissue from the distal region into a proximal region of the inner sleeve lumen. Typically, the proximal region of the inner sleeve lumen has a cross-sectional area which is larger than that of the distal region of the inner sleeve lumen. This enlargement of the lumen allows the tissue to be extracted, typically by a partial vacuum applied at a proximal end of the lumen, with a reduced risk of becoming caught or captured. Usually, the displacement member is fixedly attached to the outer sleeve and axially aligned with the distal portion of the inner sleeve lumen so that the captured tissue is engaged and pushed proximally into the proximal portion of the inner sleeve as the inner sleeve is advanced fully into the outer sleeve. In other specific embodiments, the inner sleeve is advanced over a first stroke portion which advances a tissue-cutting end of the inner sleeve across the window and then further advanced over a second stroke portion which causes the tissue-cutting end to move beyond the window. The length of the second stroke portion is at least 5% of the combined lengths of the first and second stroke portions.

BRIEF DESCRIPTION OF DRAWINGS

FIG. 8 is a schematic view of a distal end portion of another embodiment of inner RF cutting sleeve.

FIG. 9A is a cross sectional view of the RF cutting sleeve of FIG. 8 taken along line 9A-9A of FIG. 8.

FIG. 9B is a cross sectional view of the RF cutting sleeve of FIG. 8 taken along line 9B-9B of FIG. 8.

DETAILED DESCRIPTION

Figure 1:
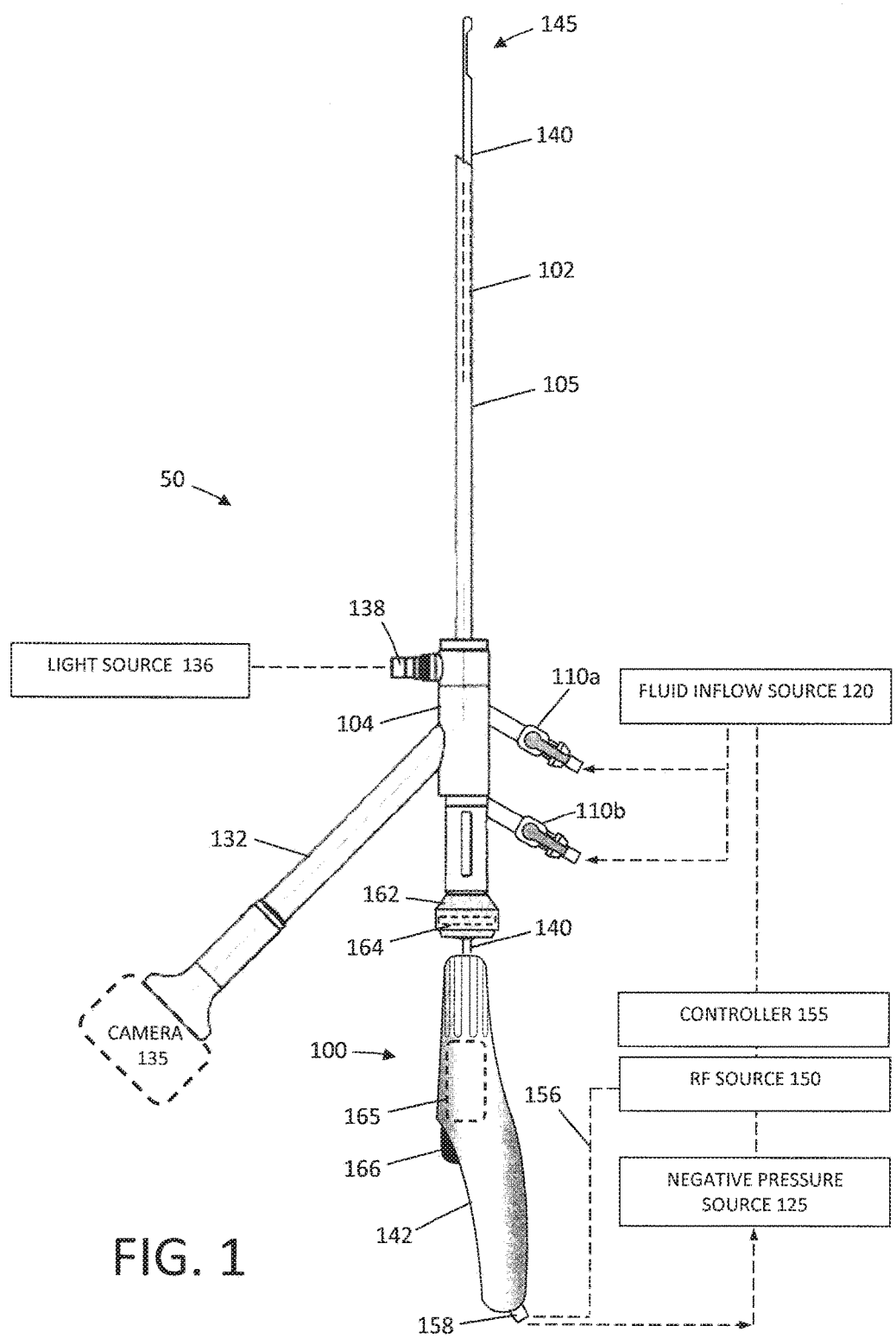
FIG. 1 is a plan view of an assembly including a hysteroscope and a tissue-cutting device corresponding to the invention that is inserted through the working channel of the hysteroscope.
Figure 2:
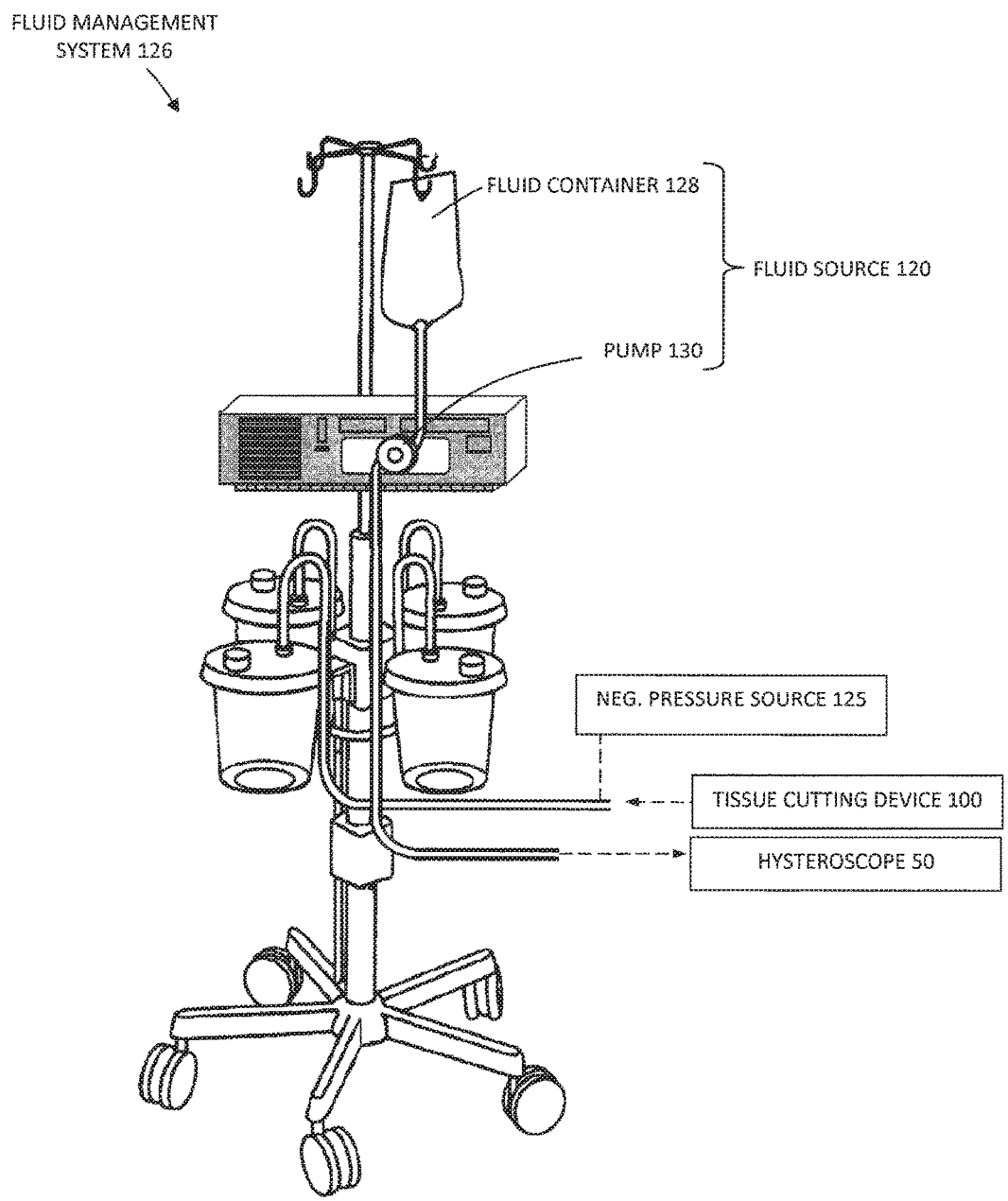
FIG. 2 is a schematic perspective view of a fluid management system used for distending the uterus and for assisting in electrosurgical tissue cutting and extraction.
Figure 3:
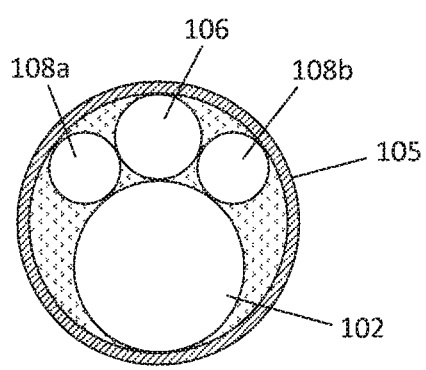
FIG. 3 is a cross-sectional view of the shaft of the hysteroscope of FIG. 1 showing various channels therein.

FIG. 1 illustrates an assembly that comprises an endoscope 50 used for hysteroscopy together with a tissue-extraction device 100 extending through a working channel 102 of the endoscope. The endoscope or hysteroscope 50 has a handle 104 coupled to an elongated shaft 105 having a diameter of 5 mm to 7 mm. The working channel 102 therein may be round, D-shaped or any other suitable shape. The endoscope shaft 105 is further configured with an optics channel 106 and one or more fluid inflow/outflow channels 108a, 108b (FIG. 3) that communicate with valve-connectors 110a, 110b configured for coupling to a fluid inflow source 120 thereto, or optionally a negative pressure source 125 (FIGS. 1-2). The fluid inflow source 120 is a component of a fluid management system 126 as is known in the art (FIG. 2) which comprises a fluid container 128 and pump mechanism 130 which pumps fluid through the hysteroscope 50 into the uterine cavity. As can be seen in FIG. 2, the fluid management system 126 further includes the negative pressure source 125 (which can comprise an operating room wall suction source) coupled to the tissue-cutting device 100. The handle 104 of the endoscope includes the angled extension portion 132 with optics to which a videoscopic camera 135 can be operatively coupled. A light source 136 also is coupled to light coupling 138 on the handle of the hysteroscope 50. The working channel 102 of the hysteroscope is configured for insertion and manipulation of the tissue-cutting and extracting device 100, for example to treat and remove fibroid tissue. In one embodiment, the hysteroscope shaft 105 has an axial length of 21 cm, and can comprise a 0° scope, or 15° to 30° scope.

Still referring to FIG. 1, the tissue-cutting device 100 has a highly elongated shaft assembly 140 configured to extend through the working channel 102 in the hysteroscope. A handle 142 of the tissue-cutting device 100 is adapted for manipulating the electrosurgical working end 145 of the device. In use, the handle 142 can be manipulated both rotationally and axially, for example, to orient the working end 145 to cut targeted fibroid tissue. The tissue-cutting device 100 has subsystems coupled to its handle 142 to enable electrosurgical cutting of targeted tissue. A radio frequency generator or RF source 150 and controller 155 are coupled to at least one RF electrode carried by the working end 145 as will be described in detail below. In one embodiment shown in FIG. 1, an electrical cable 156 and negative pressure source 125 are operatively coupled to a connector 158 in handle 142. The electrical cable couples the RF source 150 to the electrosurgical working end 145. The negative pressure source 125 communicates with a tissue-extraction channel 160 in the shaft assembly 140 of the tissue extraction device 100 (FIG. 4A).

FIG. 1 further illustrates a seal housing 162 that carries a flexible seal 164 carried by the hysteroscope handle 104 for sealing the shaft 140 of the tissue-cutting device 100 in the working channel 102 to prevent distending fluid from escaping from a uterine cavity.

In one embodiment as shown in FIG. 1, the handle 142 of tissue-cutting device 100 includes a motor drive 165 for reciprocating or otherwise moving a cutting component of the electrosurgical working end 145 as will be described below. The handle 142 optionally includes one or more actuator buttons 166 for actuating the device. In another embodiment, a footswitch can be used to operate the device. In one embodiment, the system includes a switch or control mechanism to provide a plurality of reciprocation speeds, for example 1 Hz, 2 Hz, 3 Hz, 4 Hz and up to 8 Hz. Further, the system can include a mechanism for moving and locking the reciprocating cutting sleeve in a non-extended position and in an extended position. Further, the system can include a mechanism for actuating a single reciprocating stroke.

Figure 4A:
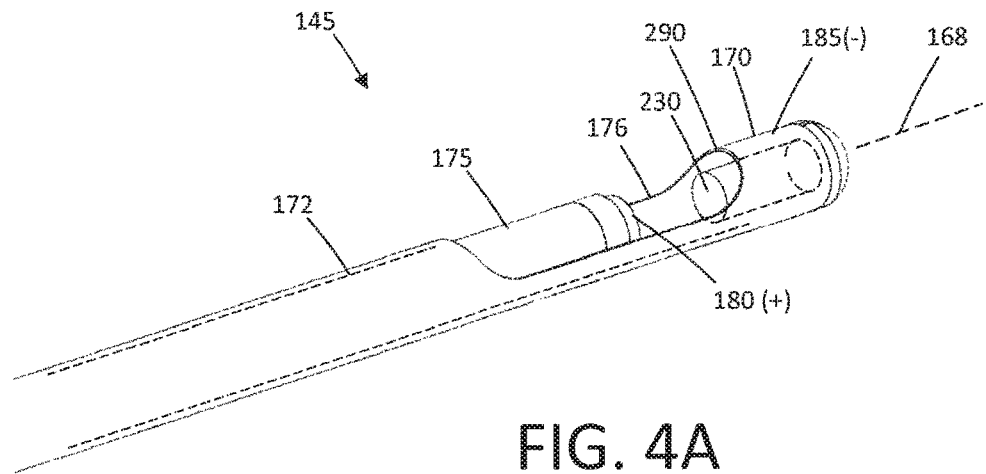
FIG. 4A is a schematic view of the working end of the electrosurgical tissue-cutting device of FIG. 1 showing an outer sleeve with a reciprocating inner cutting sleeve in a partially advanced position.

Referring to FIGS. 1 and 4A, an electrosurgical tissue-cutting device has an elongate shaft assembly 140 extending about longitudinal axis 168 comprising an exterior or first outer sleeve 170 with passageway or lumen 172 therein that accommodates a second or inner sleeve 175 that can reciprocate (and optionally rotate or oscillate) in lumen 172 to cut tissue as is known in that art of such tubular cutters. In one embodiment, the tissue-receiving window 176 in the outer sleeve 170 has an axial length ranging between 10 mm and 30 mm and extends in a radial angle about outer sleeve 170 from about 45° to 210° relative to axis 168 of the sleeve. The outer and inner sleeves 170 and 175 can comprise a thin-wall stainless steel material and function as opposing polarity electrodes as will be described in detail below. FIGS. 6A-8 illustrate insulative layers carried by the outer and inner sleeves 170 and 175 to limit, control and/or prevent unwanted electrical current flows between certain portions of the sleeve. In one embodiment, a stainless steel outer sleeve 170 has an O.D. of 0.143" with an I.D. of 0.133" and with an inner insulative layer (described below) the sleeve has a nominal I.D. of 0.125". In this embodiment, the stainless steel inner sleeve 175 has an O.D. of 0.120" with an I.D. of 0.112". The inner sleeve 175 with an outer insulative layer has a nominal O.D. of about 0.123" to 0.124" to reciprocate in lumen 172. In other embodiments, outer and or inner sleeves can be fabricated of metal, plastic, ceramic of a combination thereof. The cross-section of the sleeves can be round, oval or any other suitable shape.

As can be seen in FIG. 4A, the distal end 177 of inner sleeve 175 comprises a first polarity electrode with distal cutting electrode edge 180 about which plasma can be generated. The electrode edge 180 also can be described as an active electrode during tissue cutting since the electrode edge 180 then has a substantially smaller surface area than the opposing polarity or return electrode. In one embodiment in FIG. 4A, the exposed surfaces of outer sleeve 170 comprises the second polarity electrode 185, which thus can be described as the return electrode since during use such an electrode surface has a substantially larger surface area compared to the functionally exposed surface area of the active electrode edge 180.

Figure 5:
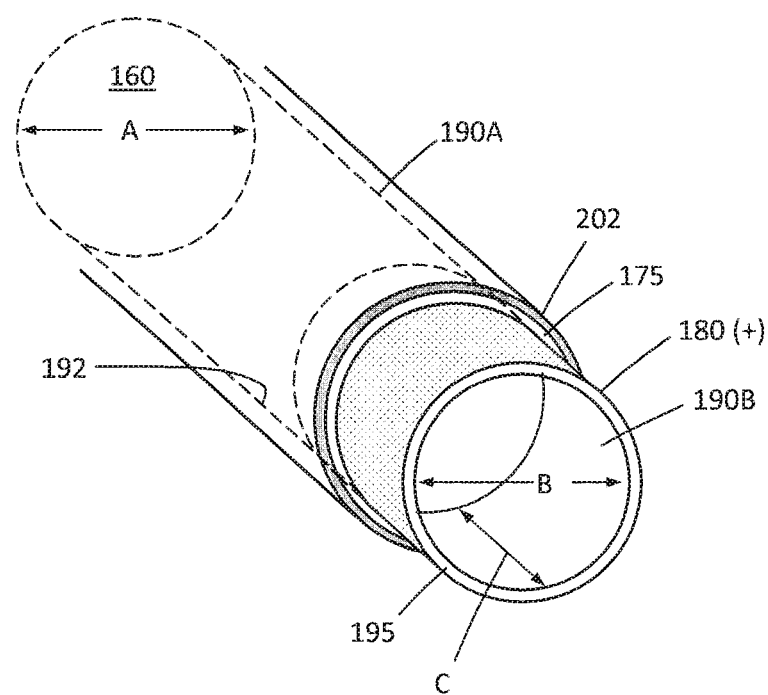
FIG. 5 is a schematic perspective view of the working end of the inner sleeve of FIG. 4 showing its electrode edge.
Figure 6A:
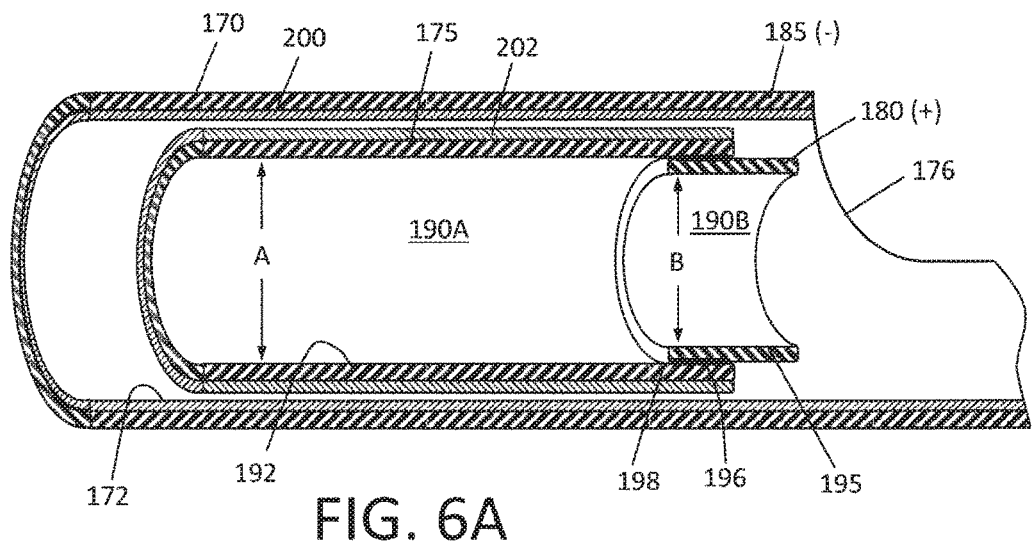
FIG. 6A is a schematic cut-away view of a portion of outer sleeve, inner RF cutting sleeve and a tissue-receiving window of the outer sleeve.

In one aspect of the invention, the inner sleeve or cutting sleeve 175 has an interior tissue extraction lumen 160 with first and second interior diameters that are adapted to electrosurgically cut tissue volumes rapidly—and thereafter consistently extract the cut tissue strips through the highly elongated lumen 160 without clogging. Referring to FIGS. 5 and 6A, it can be seen that the inner sleeve 175 has a first diameter portion 190A that extends from the handle 142 (FIG. 1) to a distal region 192 of the sleeve 175 wherein the tissue extraction lumen transitions to a smaller second diameter lumen 190B with a reduced diameter indicated at B which is defined by the electrode sleeve element 195 that provides cutting electrode edge 180. The axial length C of the reduced cross-section lumen 190B can range from about 2 mm to 20 mm. In one embodiment, the first diameter A is 0.112" and the second reduced diameter B is 0.100". As shown in FIG. 5, the inner sleeve 175 can be an electrically conductive stainless steel and the reduced diameter electrode portion also can comprise a stainless steel electrode sleeve element 195 that is welded in place by weld 196 (FIG. 6A). In another alternative embodiment, the electrode and reduced diameter electrode sleeve element 195 comprises a tungsten tube that can be press fit into the distal end 198 of inner sleeve 175. FIGS. 5 and 6A further illustrates the interfacing insulation layers 202 and 204 carried by the first and second sleeves 170, 175, respectively. In FIG. 6A, the outer sleeve 170 is lined with a thin-wall insulative material 200, such as PFA, or another material described below. Similarly, the inner sleeve 175 has an exterior insulative layer 202. These coating materials can be lubricious as well as electrically insulative to reduce friction during reciprocation of the inner sleeve 175.

The insulative layers 200 and 202 described above can comprise a lubricious, hydrophobic or hydrophilic polymeric material. For example, the material can comprise a bio-compatible material such as PFA, TEFLON®, polytetrafluroethylene (PTFE), FEP (Fluorinated ethylenepropylene), polyethylene, polyamide, ECTFE (Ethylenechlorotrifluoroethylene), ETFE, PVDF, polyvinyl chloride or silicone.

Figure 6B:
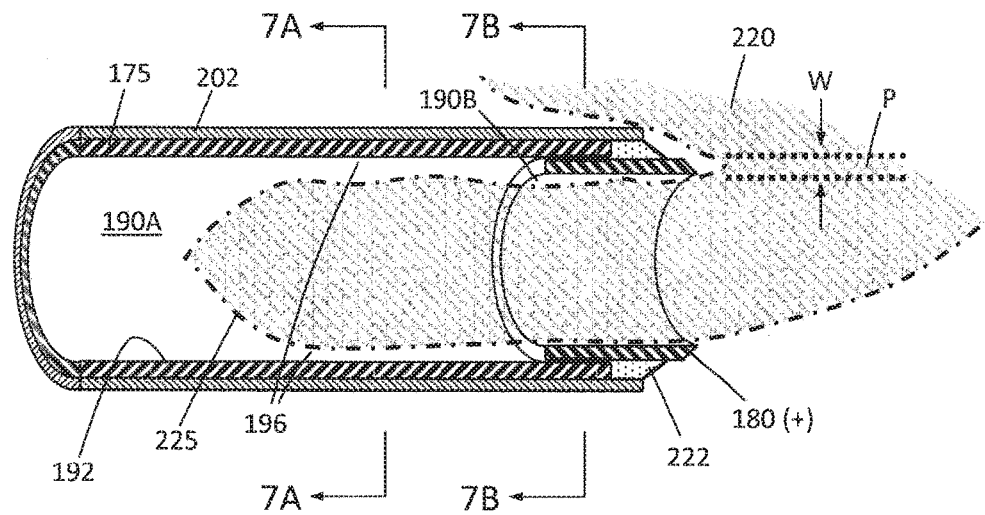
FIG. 6B is a schematic view of a distal end portion another embodiment of inner RF cutting sleeve.

Now turning to FIG. 6B, another variation of inner sleeve 175 is illustrated in a schematic view together with a tissue volume being resected with the plasma electrode edge 180. In this embodiment, as in other embodiments in this disclosure, the RF source operates at selected operational parameters to create a plasma around the electrode edge 180 of electrode sleeve 195 as is known in the art. Thus, the plasma generated at electrode edge 180 can cut and ablate a path P in the tissue 220, and is suited for cutting fibroid tissue and other abnormal uterine tissue. In FIG. 6B, the distal portion of the cutting sleeve 175 includes a ceramic collar 222 which is adjacent the distal edge 180 of the electrode sleeve 195. The ceramic 222 collar functions to confine plasma formation about the distal electrode edge 180 and functions further to prevent plasma from contacting and damaging the polymer insulative layer 202 on the cutting sleeve 175 during operation. In one aspect of the invention, the path P cut in the tissue 220 with the plasma at electrode edge 180 provides a path P having an ablated width indicated at W, wherein such path width W is substantially wide due to tissue vaporization. This removal and vaporization of tissue in path P is substantially different than the effect of cutting similar tissue with a sharp blade edge, as in various prior art devices. A sharp blade edge can divide tissue (without cauterization) but applies mechanical force to the tissue and may prevent a large cross section slug of tissue from being cut. In contrast, the plasma at the electrode edge 180 can vaporize a path P in tissue without applying any substantial force on the tissue to thus cut larger cross sections or slugs of strips of tissue. Further, the plasma cutting effect reduces the cross section of tissue strip 225 received in the tissue-extraction lumen 190B. FIG. 6B depicts a tissue strip to 225 entering lumen 190B which has such a smaller cross-section than the lumen due to the vaporization of tissue. Further, the cross section of tissue 225 as it enters the larger cross-section lumen 190A results in even greater free space 196 around the tissue strip 225. Thus, the resection of tissue with the plasma electrode edge 180, together with the lumen transition from the smaller cross-section (190B) to the larger cross-section (190A) of the tissue-extraction lumen 160 can significantly reduce or eliminate the potential for successive resected tissue strips 225 to clog the lumen. Prior art resection devices with such small diameter tissue-extraction lumen typically have problems with tissue clogging.

In another aspect of the invention, the negative pressure source 225 coupled to the proximal end of tissue-extraction lumen 160 (see FIGS. 1 and 4A) also assists in aspirating and moving tissue strips 225 in the proximal direction to a collection reservoir (not shown) outside the handle 142 of the device.

Figures 7A, 7B:
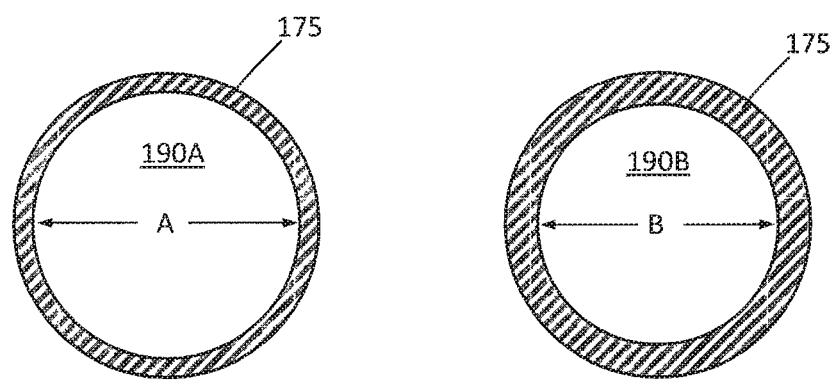
FIG. 7A is a cross sectional view of the inner RF cutting sleeve of FIG. 6B taken along line 7A-7A of FIG. 6B.
FIG. 7B is another cross sectional view of the inner RF cutting sleeve of FIG. 6B taken along line 7B-7B of FIG. 6B.

FIGS. 7A-7B illustrate the change in lumen diameter of cutting sleeve 175 of FIG. 6B. FIG. 8 illustrates the distal end of a variation of cutting sleeve 175' which is configured with an electrode cutting element 195' that is partially tubular in contrast to the previously described tubular electrode element 195 (FIGS. 5 and 6A). FIGS. 9A-9B again illustrate the change in cross-section of the tissue-extraction lumen between reduced cross-section region 190B' and the increased cross-section region 190A' of the cutting sleeve 175' of FIG. 8. Thus, the functionality remains the same whether the cutting electrode element 195' is tubular or partly tubular. In FIG. 8, the ceramic collar 222' is shown, in one variation, as extending only partially around sleeve 175 to cooperate with the radial angle of cutting electrode element 195'. Further, the variation of FIG. 8 illustrates that the ceramic collar 222' has a larger outside diameter than insulative layer 202. Thus, friction may be reduced since the short axial length of the ceramic collar 222' interfaces and slides against the interfacing insulative layer 200 about the inner surface of lumen 172 of outer sleeve 170.

In general, one aspect of the invention comprises a tissue cutting and extracting device (FIGS. 4A-4B) that includes first and second concentric sleeves having an axis and wherein the second (inner) sleeve 175 has an axially-extending tissue-extraction lumen therein, and wherein the second sleeve 175 is moveable between axially non-extended and extended positions relative to a tissue-receiving window 176 in first sleeve 170 to resect tissue, and wherein the tissue extraction lumen 160 has first and second cross-sections. The second sleeve 175 has a distal end configured as a plasma electrode edge 180 to resect tissue disposed in tissue-receiving window 176 of the first sleeve 170. Further, the distal end of the second sleeve, and more particularly, the electrode edge 180 is configured for plasma ablation of a substantially wide path in the tissue. In general, the tissue-extraction device is configured with a tissue extraction lumen 160 having a distal end portion with a reduced cross-section that is smaller than a cross-section of medial and proximal portions of the lumen 160.

In one aspect of the invention, referring to FIGS. 7A-7B and 9A-9B, the tissue-extraction lumen 160 has a reduced cross-sectional area in lumen region 190A proximate the plasma cutting tip or electrode edge 180 wherein said reduced cross section is less than 95%, 90%, 85% or 80% than the cross sectional area of medial and proximal portions 190B of the tissue-extraction lumen, and wherein the axial length of the tissue-extraction lumen is at least 10 cm, 20 cm, 30 cm or 40 cm. In one embodiment of tissue-cutting device 100 for hysteroscopic fibroid cutting and extraction (FIG. 1), the shaft assembly 140 of the tissue-cutting device is 35 cm in length.

Figure 4B:
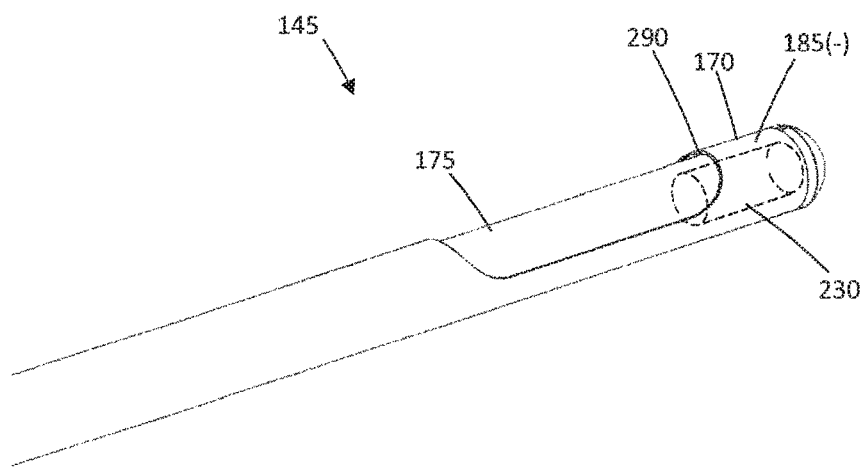
FIG. 4B is a schematic view of the working end of FIG. 4A with the reciprocating inner cutting sleeve in a fully advanced position.
Figure 10:
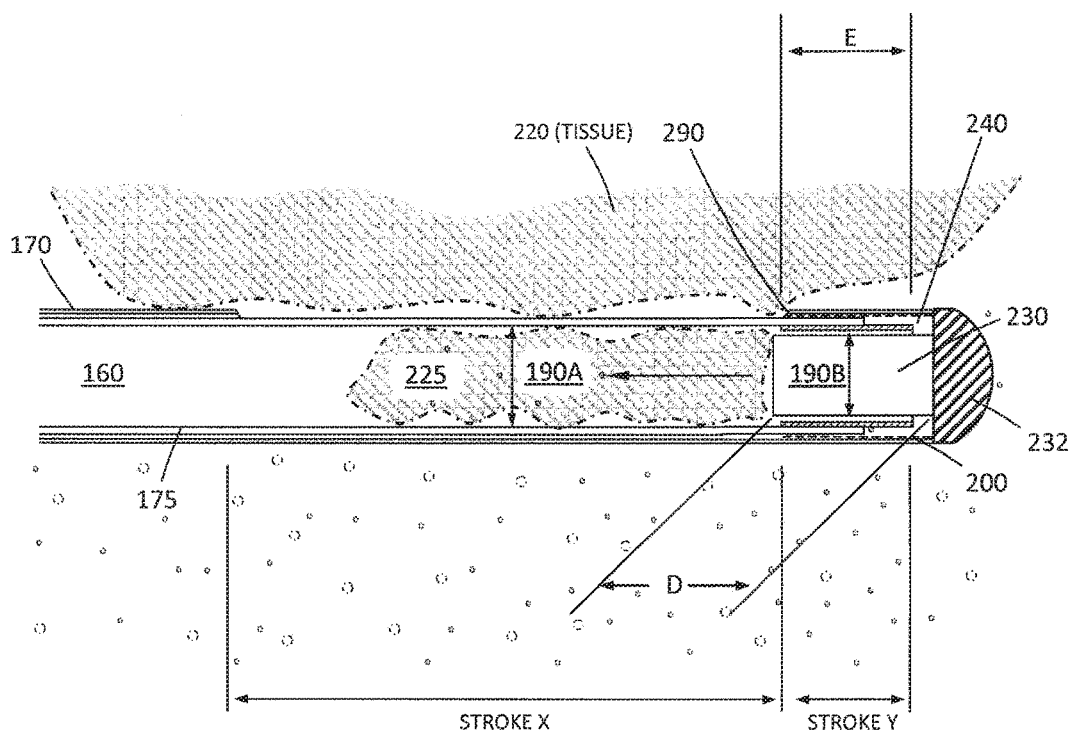
FIG. 10 is an enlarged cross sectional view of a working end with an RF cutting sleeve in advanced position and a tissue displacement member pushing a tissue strip proximally in the extraction lumen.

Now referring to FIGS. 4A-4B and FIG. 10, one aspect of the invention comprises a "tissue displacement" mechanism that is configured to displace and move tissue strips 225 (see FIG. 10) in the proximal direction in lumen 160 of cutting sleeve 175 to thus ensure that tissue does not clog the lumen of the inner sleeve 175. As can be seen in FIGS. 4A, 4B and 10, one tissue displacement mechanism comprises a projecting element 230 that extends proximally from distal tip or body 232 that is fixedly attached to outer sleeve 170. The projecting element 230 extends proximally along central axis 168 in a distal chamber 240 defined by outer sleeve 170 and the interior surface of the distal tip 232. In one embodiment depicted in FIGS. 4A and 10, the shaft-like projecting element 230 thus functions as a plunger or pusher member and can push a captured tissue strip 225 in the proximal direction from the small cross-section lumen 190B of cutting sleeve 175 as the cutting sleeve 175 moves to its fully advanced or extended position (see. FIG. 10). For this reason, the length D of the projecting element 230 is at least as great as the axial length E of the small cross-section lumen 190B in the cutting sleeve. Further, as depicted in FIG. 10, the stroke Y of the cutting sleeve 175 extends at least about 3 mm, 4 mm or 5 mm distally beyond the distal edge of the window 290. In another aspect, the stroke Y of the cutting sleeve 175 is at least 5% or 10% of the total stroke of the cutting sleeve (stroke X+stroke Y in FIG. 10).

In general, a method of cutting tissue corresponding to the invention comprising cutting tissue with a reciprocating cutting sleeve having an extending stroke and a retracting stroke within an outer sleeve, wherein the extending stroke cuts and captures tissue received by a tissue-receiving window in the outer sleeve, and pushing the captured tissue in the proximal direction in the cutting sleeve with a displacement member when the cutting sleeve is in a transition range in which the cutting sleeve transitions from the extending stroke to the retracting stroke. Further, the displacement member is configured to push the captured tissue at least in part from a first smaller cross-section lumen to a second larger cross-section lumen in the cutting sleeve. Thereafter, the negative pressure source can more effectively extract and aspirate the tissue from the lumen.

In another aspect of the invention, the tissue cutting device comprises an elongated assembly comprising concentric outer and inner sleeves, with a tissue-receiving window in the outer sleeve open to an interior lumen with a distal lumen portion extending distal to the window, wherein the inner sleeve is configured with a first axially-extending channel having a lesser cross-sectional area and a second axially-extending channel portion having a second greater cross-sectional area and wherein the ratio of lengths of the distal lumen portion relative to the first channel is at least 1:1. In one embodiment, the device is configured with a length of the distal lumen portion that is at least 5 mm. In this embodiment, the length of first axially-extending channel is at least 5 mm.

In another aspect of the invention, a tissue cutting device is comprised of an elongated assembly comprising concentric outer and inner sleeves, with a tissue-receiving window in the outer sleeve open to an interior lumen with a distal lumen portion extending distal to the window, wherein the ratio of the length of the distal lumen portion relative to the diameter of the interior lumen is at least 1:1. In one embodiment, the ratio is at least 1.5:1. In this embodiment, the length of the distal lumen portion is at least 5 mm. In one variation, the diameter of the interior lumen is less than 5 mm.

In general, a tissue cutting device comprised of a handle coupled to an elongated tubular assembly comprising outer and inner concentric sleeves, a tissue-receiving window in the outer sleeve communicating with an interior passageway extending through the assembly wherein a distal edge of the window is a spaced at least 4 mm, 6 mm, 8 mm or 10 mm from the distal end of the interior passageway. In this variation, the mean cross section of the passageway is less than 5 mm, 4 mm or 3 mm.

One embodiment of a tissue cutting device comprises a handle coupled to an axially-extending shaft assembly defining a tissue-receiving window communicating with an interior extraction lumen for extracting tissue, the shaft assembly comprising axially-extending first and second elements with at least one element axially moveable relative to the other element between a first position and a second position, and a displacement feature configured to displace resected tissue from the extraction lumen. In this embodiment, the first position comprises an open-window configuration for receiving tissue therein and the second position is a closed-window configuration. The movement of the elements from the first position toward the second position cuts tissue with a cutting edge of an element. The cutting edge can comprise a sharp blade edge or an RF electrode edge. The displacement feature (FIG. 4A) or projecting element 230 can be coupled to the first element, can project axially relative to an axis of the extraction lumen. This embodiment is configured with an extraction lumen having first and second cross-sectional areas, wherein a distal region of the extraction lumen has a first lesser cross-sectional area and a medial portion of the extraction lumen has a second greater cross-sectional area. In one variation, the distal region of the extraction lumen having the first cross-sectional area extends axially at least 2 mm, 4 mm, 6 mm and 8 mm. In another variation, the displacement feature is configured to extend axially into the extraction lumen in the second closed-window configuration at least 2 mm, 4 mm, 6 mm and 8 mm.

Figure 11:
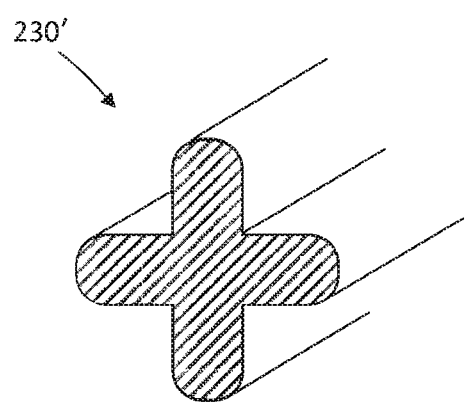
FIG. 11 is a cross-sectional of a variation of the tissue displacement member of FIG. 10.

In general, the displacement feature or projecting element 230 has a maximum cross-section that extends substantially across a cross-section of the extraction lumen. In one variation, the displacement feature has a cross-sectional area that substantially occupies the first cross-sectional area of the extraction lumen. FIGS. 4A and 10 illustrate a projecting element 230 that is cylindrical. FIG. 11 illustrates a section of a projecting element 230' that has a symmetric shape relative to a central axis of the extraction lumen, and is star-shaped or fluted with ribs and channels to allow distension fluid to flow therethrough as the cutting sleeve 175 reciprocates in chamber 240. In another embodiment, the projecting element can have an asymmetric cross sectional shape with any number or flutes, grooves, lumens or bore extending about its axis. In a typical embodiment, the projecting element 230 is a dielectric such as a ceramic or polymer.

Figure 12:
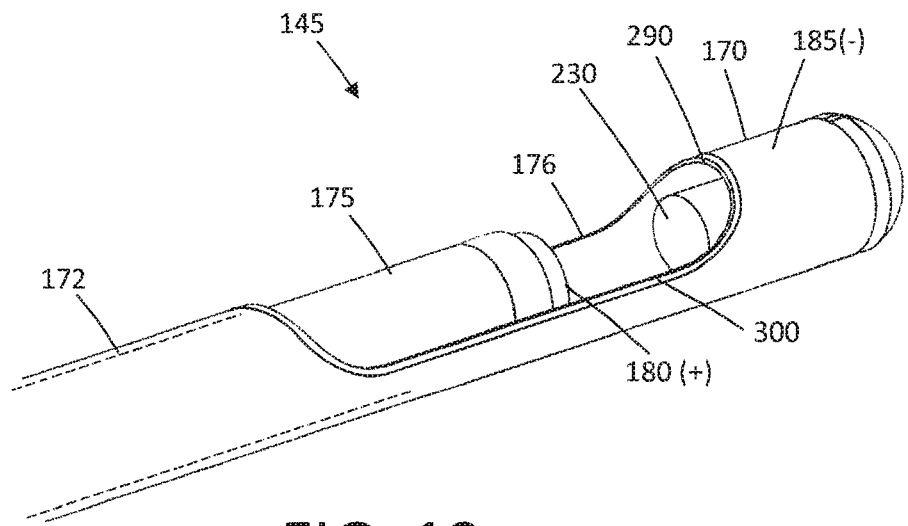
FIG. 12 is a perspective view of another embodiment of working end having a tissue-receiving window with a dielectric edge.
Figure 13:
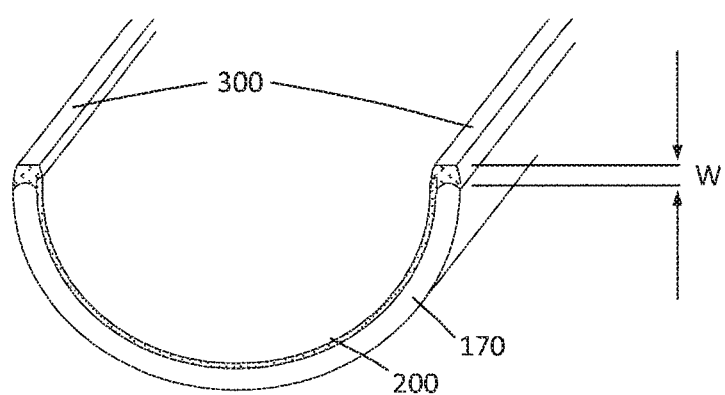
FIG. 13 is a cross section of the tissue-receiving window of FIG. 12 showing the dielectric edge and interior dielectric layer.

In another embodiment depicted in FIGS. 12-13, the tissue cutting device again comprises an elongated assembly comprising concentric outer and inner sleeves, with a tissue-receiving window in the outer sleeve open to an interior lumen. In this embodiment, the edges of the window comprise a dielectric element 300 such as a polymer or ceramic that can be molded, formed and bonded around the edge of window 176 in the metal sleeve 170. This prevents unwanted arcing from the electrode edge 180 to the exterior of sleeve 170 (or electrode 185) when plasma is generated at the electrode edge 180 during reciprocation. The width W (FIG. 13) of the dielectric is at least 0.005". FIG. 13 illustrates a sectional view of an outer sleeve 170 at the window 176 comprising a conductive electrode and dielectric element 300 around the edge of the window. It can be seen that thin insulative layer 200 is configured to join and bond to the dielectric element 300.

Figure 14:
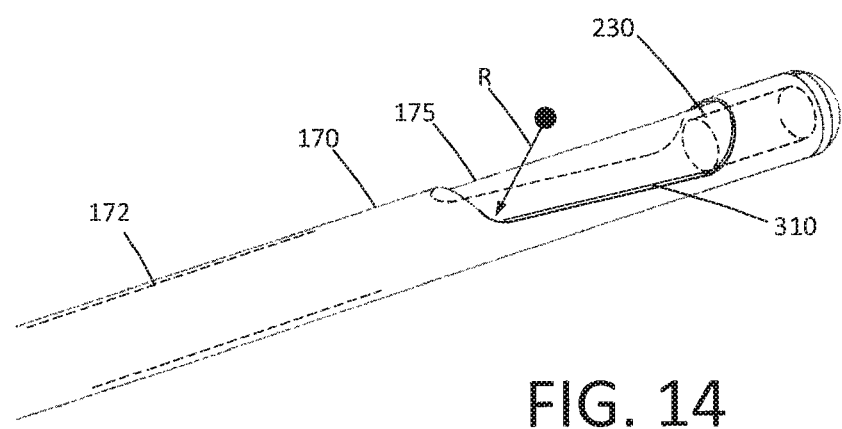
FIG. 14 is a perspective view of another embodiment of working end with a tissue-receiving window that has an asymmetric configuration.

FIG. 14 depicts the working end of another embodiment of tissue cutting device similar to those described above with a window 310 opening to the interior bore 172 of outer sleeve 170 wherein the longitudinal window 310 is longitudinally asymmetrical and wherein the window depth increases in the distal direction. As can be understood from FIG. 10, the asymmetric window 310 of FIG. 13 draws a lesser volume tissue into the proximal window portion and a greater volume of tissue into the distal window portion for cutting with electrode edge 190. Thus, this window configuration allows for a lesser cross section of tissue strip 225 in the proximal direction and a greater cross section of tissue strip 225 in the distal direction. The variation in cross-section of the captured tissue increases the efficiency of the negative pressure source 225 (FIG. 1) in applying effective aspiration forces on the tissue strip 225 in the lumen, which is further assisted by projecting member 230 which is configured to push the distal, greater cross-sectional end of tissue strip 225 in the lumen 160 of inner sleeve 175.

Further, still referring to FIG. 14, the increased radius R allowed by the varied depth window 310 allow for greater strength of the assembly in the proximal region of the window as the outer sleeve 270 transitions to the full hoop strength of the sleeve.

Figure 15:
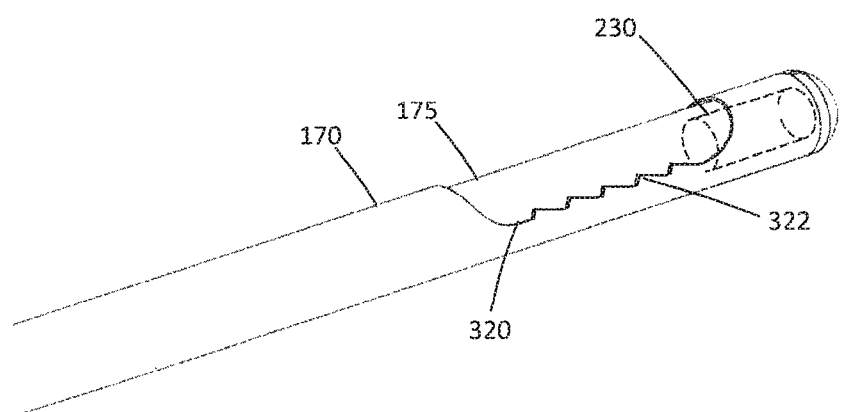
FIG. 15 is a perspective view of another variation with a tissue-receiving window that is configured with tissue-gripping features.

FIG. 15 depicts another working end variation similar to those described above with a window 320 opening to interior bore 172 of outer sleeve 170. In this embodiment, the longitudinal window 320 has an edge configured with gripping features 322 such as teeth or an abrasive surface which assist in maintaining tissue 220 (see FIG. 10) in a non-sliding disposition as the cutting sleeve 175 is moving in its extending stroke.

Figure 16:
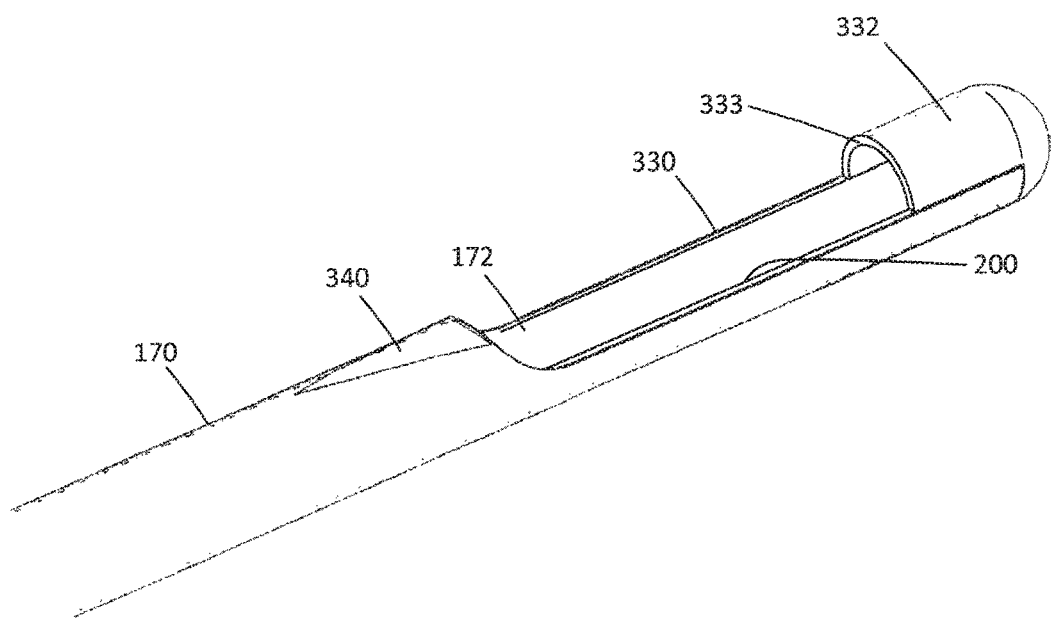
FIG. 16 is a perspective view of another variation with an exterior sleeve with a distal dielectric body portion.

FIG. 16 depicts another working end variation similar to those described above with a window 330 opening to interior bore 172 of outer sleeve 170. In this embodiment, a distal body 332 of a dielectric is bonded to the sleeve to thus provide distal window edge 333 that is entirely of non-conductive material. The body 332 can comprise a ceramic or polymeric material that is useful in preventing plasma at the reciprocating electrode edge 180 (see FIG. 10) of the cutting sleeve 170 from folding, flexing, abrading, delaminating or otherwise damaging the dielectric lining or layer 200 laminated in bore 172 of sleeve 170.

FIG. 16 further depicts a marking 340 that marks the proximal end of window 320 opening to interior bore 172 of outer sleeve 170. This marking is useful for orienting and to rotating the working end 145 when viewing through the hysteroscope and the physician presses the window into contact with tissue. Further, the working end has another marker (not visible) on the exterior of outer sleeve 180 to further orient the physician to the window.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A tissue resecting device, comprising:
    an outer sleeve having a tissue-receiving window opening into a lumen of the outer sleeve; and
    an axially reciprocating inner sleeve disposed within the lumen of the outer sleeve, the inner sleeve having a lumen and a tissue-resecting distal end, the inner sleeve being configured to move longitudinally between an open window position and a closed window position;
    wherein the outer sleeve includes a distal tip fixedly attached to a distal end of the outer sleeve and a projecting element extending proximally from the distal tip;
    wherein the projecting element is disposed distal of the lumen of the inner sleeve in the open window position and extends into the lumen of the inner sleeve in the closed window position;
    wherein the tissue-receiving window is longitudinally asymmetrical.

2. The tissue resecting device of claim 1, wherein a depth of the tissue-receiving window from an outer surface of the outer sleeve varies along a length of the tissue-receiving window.

3. The tissue resecting device of claim 2, wherein the depth of the tissue-receiving window increases in a distal direction.

4. The tissue resecting device of claim 1, wherein the tissue-resecting distal end has a first cross-sectional area less than a second cross-sectional area at a portion of the inner sleeve proximal of the tissue-resecting distal end.

5. The tissue resecting device of claim 4, wherein the projecting element has a maximum cross-sectional area that extends substantially across the first cross-sectional area.

6. The tissue resecting device of claim 1, wherein the projecting element has a substantially symmetric shape.

7. The tissue resecting device of claim 1, wherein the projecting element comprises ribs and channels extending longitudinally.

8. The tissue resecting device of claim 1, wherein the lumen of the inner sleeve is in fluid communication with a negative pressure source configured to aspirate resected tissue therethrough.

9. The tissue resecting device of claim 1, wherein an edge of the tissue-receiving window is configured with gripping features.

10. The tissue resecting device of claim 9, wherein the edge includes teeth or an abrasive surface.

11. A tissue resecting device, comprising:
    an outer sleeve having a longitudinally asymmetrical tissue-receiving window opening into a lumen of the outer sleeve; and
    an inner sleeve slidably disposed within the lumen of the outer sleeve and having a tissue-resecting distal end, wherein a lumen of the inner sleeve is in fluid communication with a negative pressure source configured to aspirate resected tissue through the lumen of the inner sleeve;
    wherein the outer sleeve includes a distal tip fixedly attached to a distal end of the outer sleeve and a tissue displacement feature extending proximally from the distal tip within the lumen of the outer sleeve;
    wherein the tissue displacement feature extends proximal of a distal end of the tissue-receiving window;
    wherein the inner sleeve moves longitudinally relative to the tissue displacement feature.

12. The tissue resecting device of claim 11, wherein the inner sleeve has a first cross-sectional area extending from a proximal end of the inner sleeve to a distal region of the inner sleeve.

13. The tissue resecting device of claim 12, wherein the tissue-resecting distal end defines a second cross-sectional area smaller than the first cross-sectional area.

14. The tissue resecting device of claim 13, wherein a length of the tissue displacement feature is at least as long as an axial length of the second cross-sectional area defined by the tissue-resecting distal end.

15. The tissue resecting device of claim 11, wherein a distal portion of the tissue-receiving window defines a larger opening into the lumen of the outer sleeve than a proximal portion of the tissue-receiving window.

16. A tissue resecting device, comprising:
an outer sleeve having a tissue-receiving window opening into a lumen of the outer sleeve; and
an inner sleeve slidably disposed within the lumen of the outer sleeve and configured to shift longitudinally between an open window position and a closed window position, the inner sleeve having a tissue-resecting distal end and an interior lumen in fluid communication with a negative pressure source for aspiration of resected tissue through the interior lumen;
wherein the outer sleeve includes a closed distal tip at a distal end of the outer sleeve and a tissue displacement feature extending proximally from the closed distal tip;
wherein the tissue displacement feature is fixed relative to the outer sleeve;
wherein a proximal end of the tissue displacement feature is located proximal of a distal end of the tissue-receiving window and a distal end of the tissue displacement feature is located distal of the distal end of the tissue-receiving window;
wherein the tissue-receiving window extends around a portion of a circumference of the outer sleeve, and a distal portion of the tissue-receiving window extends further around the circumference of the outer sleeve than a proximal portion of the tissue-receiving window.

17. The tissue resecting device of claim 16, wherein the tissue-resecting distal end extends distally of the distal end of the tissue-receiving window in the closed window position.

18. The tissue resecting device of claim 17, wherein the tissue displacement feature extends into the interior lumen of the inner sleeve in the closed window position.

19. The tissue resecting device of claim 16, wherein the tissue-resecting distal end includes an RF electrode operatively coupled to an RF source configured to create a plasma around an edge of the RF electrode.

20. The tissue resecting device of claim 16, further comprising a motor drive configured to axially reciprocate the inner sleeve between the open window position and the closed window position.

* * * * *